US005200341A

United States Patent [19]
Obukowicz

[11] Patent Number: 5,200,341
[45] Date of Patent: Apr. 6, 1993

[54] ALTERED GENE AND *E. COLI* STRAINS AND METHODS USEFUL IN ENHANCED ACCUMULATION OF PROTEINS

[75] Inventor: Mark G. Obukowicz, St. Charles, Mo.

[73] Assignee: Monsanto Company, St. Louis, Mo.

[21] Appl. No.: 772,760

[22] Filed: Oct. 7, 1991

[51] Int. Cl.$^5$ .................. C12N 15/31; C12N 1/21; C12N 15/67; C12P 21/00

[52] U.S. Cl. ..................... 435/252.33; 435/252.8; 435/69.1; 536/23.51

[58] Field of Search ............... 435/69.1, 183, 252.33, 435/252.8; 536/27

[56] References Cited

FOREIGN PATENT DOCUMENTS 0216747 4/1987 European Pat. Off. .
WO 90/03438 4/1990 PCT Int'l Appl. .

OTHER PUBLICATIONS

Obukowicz et al. (May 1992), Appl. Environ. Microbiol. 58(5): 1511-1523.
Grossman, Alan D. et al., "Mutations in the rpoH (hptR) gene of *Escherichia coli* K-12 phenotypically suppress a temperature-sensitive mutant defective in the sigma-70 subunit of RNA polymerase", *J. Bacteriology* 161:939-943 (1985).
Calendar, Richard et al., "Deletion and insertion mutations in the rpoH Gene of *Escherichia coli* that produce functional sigma-32", *J. Bacteriology* 170:3479-3484 (1988).
Obukowicz, Mark G. et al., "Secretion and export of IGF-1 in *Escherichia coli* strain JM101", *Mol. Gen. Genet.* 215:19-25 (1988).
Silhavy, Thomas J. et al., *Experiments with Gene Fusions*, Cold Spring Harbor Laboratory, Cold Spring Harbor, N.Y. (1984).
Grossman, Alan D. et al., "Mutations in the lon gene of *E. coli* K12 phenotypically suppress a mutation in the sigma subunit of RNA polymerase," *Cell* 32:151-159 (1983).
Gierse, James K. et al., "Expression, purification, and in viro activity of atrial natriuretic factor prohormone produced in *Escherichia coli,*:" *Archiv. Biochem. Biophys.*, 271:441-446 (1989).

Wong, Edith Y. et al., "Expression of secreted insulin-like growth factor-1 in *Escherichia coli,*" *Gene* 68:193-203 (1988).
Easton, Alan M. et al., "Production of bovine insulin-like growth factor-2 (bIGF-2) in *Escherichia coli,*" *Gene* 101:291-295 (1990).
Schuler, Linda A. et al., "Bovine placental lactogen:-molecular cloning and protein structure,"*Biochemistry* 27:8443-8448 (1988).
Miller, W. L. et al., "Cloning of bovine prolactin cDNA and evolutionary implications of its sequence," *DNA* 1:37-50 (1981).
Grossman, Alan D. et al., "The hptR gene product of *E. coli* is a sigma factor for heat-shock promoters," *Cell*, vol. 38, 383-390, Sep. 1984.
Grossman, A. D. et al., "Analysis of the *Escherichia coli* heat shock response," *Microbiology*-1985, Loretta Leive (ed.), American Society for Microbiology, Washington, D.C. (1985).
Grossman, Alan D. et al., "$\sigma^{32}$ synthesis can regulate the synthesis of heat shock proteins in *Escherichia coli*", *Genes & Development*, 1:179-184, 1987.
Helmann, John D. and Chamberlin, Michael J., "Structure and Function of Bacterial Sigma Factors", *Ann. Rev. Biochem.*, 1988, 57:839-72.

(List continued on next page.)

Primary Examiner—Richard A. Schwartz
Assistant Examiner—Philip W. Carter
Attorney, Agent, or Firm—Dennis A. Bennett

[57] ABSTRACT

An rpoH gene that encodes a $\sigma^{32}$ protein in which cysteine instead of arginine is at amino acid residue 268 was isolated from a mutant of *Escherichia coli* strain W3110. The rpoH gene has thymine instead of cytosine at the nucleotide position corresponding to 802 in the wild-type rpoH gene. Purified strains of *E. coli* W3110 and JM101 having a mutant rpoH gene in which thymine instead of cytosine is at the nucleotide position corresponding to 802 in a wild-type rpoH gene and a method for synthesis of proteins at enhanced levels are also disclosed. The method comprises introducing an expression vehicle into an *E. coli* strain containing the mutant rpoH gene of this invention.

9 Claims, No Drawings

OTHER PUBLICATIONS

Straus, David et al., "DnaK, DnaJ, and GrpE heat shock proteins negatively regulate heat shock gene expression by controlling the synthesis and stability of $\sigma^{32}$", *Genes & Development*, 4:2202–2209, 1990.

Yura, Takashi and Osawa, Toshio, "Genetics Studies and Evolution of RNA Polymerase, Sigma Factor in *Escherichia coli*", pp. 51–63, *Genetics and Evolution of RNA Polymerase, trNA and Ribosomes*, Osawa, S. et al., (ed.) Univ. of Tokyo Press, Tokyo, Japan.

Hu, James C. and Gross, Carol A., "Marker Rescue with Plasmids Bearing Deletions in RpoD Identifies a dispensible part of *E. coli* sigma factor", *Mol. Gen. Genet.* 1983, 191:492–298.

Bachmann, Barbara J., "Derivations and Genotypes of Some Mutant Derivatives of *Escherichia coli* K-12", pp. 1190–1219, *Escherichia coli and Salmonella typhimurium*, Neidhardt, F. C. et al. (ed.), American Society for Microbiology, Washington, D.C. (1987).

Sambrook, J. et al., "Molecular Cloning", pp. A.1, A.3, Cold Spring Harbor Laboratory Press, 1989.

Messing, J., "A Multipurpose Cloning system based on the single-stranded DNA Bacteriophage M13", *Recombinant DNA Technical Bulletin*, NIH Publication #79-99, vol. 2, No. 2, (1979) pp. 43–48.

Maloy, Stanley R. and Nunn, William D., "Selection of Loss of Tetracycline Resistance by *Escherichia coli, Journal of Bacteriology*", Feb. 1981, pp. 1110–1112.

Yano, Ryoji et al., "A Mutation that Enhances Synthesis of $\sigma^{32}$ and Suppresses Temperature-Sensitive Growth of the rpoH15 Mutant of *Escherichia coli*", *Journal of Bacteriology*, Apr. 1990, pp. 2124–2130.

Tobe, Toru et al., "Suppression of rpoH (hptR) Mutations of *Escherichia coli*: Heat Shock Response in suhA Revertants", *Journal of Bacteriology*, Sep. 1987, pp. 4128–4134.

Tobe, Toru et al., "Isolation and Physical Mapping of Temperature-Sensitive Mutants Defective in Heat—Shock Induction of Proteins in *Escherichia coli*", *Mol. Gen. Genet.* (1984) 195:10–16.

Yura, Takashi et al., "Heat Shock Regulatory Gene (hptR) of *Escherichia coli* is Required for Growth at High Temperature But is Dispensable at Low Temperature", *Proc. Natl. Acad. Sci.* USA, vol. 81, pp. 6803–6807, Nov. 1984.

Bukau, Bernd et al., "Mutations Altering Heat Shock Specific Subunit of RNA Polymerase Suppress Major Cellular Defects of *E. coli* Mutants Lacking the DnaK Chaperone", *The EMBO Journal*, vol. 9, No. 12, pp. 4027–4038, 1990.

Baker, Tania A. et al., "A Gene Regulating the Heat Shock Response in *Escherichia coli* Also Affects Proteolysis", *Proc. Natl. Acad. Sci.* USA, vol. 81, pp. 6779–6783, Nov. 1984.

Cooper, Stephen et al., "A Temperature Sensitive Nonsense Mutation Affecting the Synthesis of a Major Protein of *Escherichia coli* K12", *Molec. Gen. Genet.* 139, 167–176 (1975).

ALTERED GENE AND E. COLI STRAINS AND METHODS USEFUL IN ENHANCED ACCUMULATION OF PROTEINS

BACKGROUND OF THE INVENTION

This invention relates to a newly isolated mutant rpoH gene, to an altered $\sigma^{32}$ protein encoded by the mutant rpoH gene, and to related E. coli strains. More particularly, the present invention relates to the use of such gene and related strains for enhanced accumulation of proteins synthesized by the gene.

The heat shock response occurs in wild-type Escherichia coli when cells are shifted abruptly from low temperature (e.g., 30° C.) to high temperature (e.g., 42° C.). Several of the heat shock proteins have been implicated in proteolysis of abnormal or heterologous proteins and thus are of applied interest. Most of the research with mutations in E. coli proteases and their effect on heterologous protein stability has involved the heat shock gene lon, encoding protease La. Protease La has been the most extensively studied protease in E. coli. In lon mutants, ATP-dependent proteolysis is reduced 2 to 4-fold. However, proteolysis is not prevented by lon mutants, even in strains which are lon null mutants, indicating that other bacterial proteases are also involved. The usefulness of lon mutants in accumulating higher levels of labile heterologous proteins appears to be marginal since, in most cases, the degradation of various heterologous proteins and peptides is not affected by lon null mutations. Exceptions, however, have been reported.

Transcription of all of the heat shock genes characterized to date is controlled by an alternate RNA polymerase sigma factor, the $\sigma^{32}$ protein, the product of the rpoH (also known as htpR) gene. The sequence of the $\sigma^{32}$ protein has been published, e.g., in Calendar et al., "Deletion and insertion mutations in the rpoH gene of Escherichia coli that produce functional sigma-32," J. Bacteriology 170:3479-3484 (1988), which publication is incorporated herein by reference. The rpoH gene has been described, e.g., in Grossman, A. D. et al., "The hptR gene product of E. coli is a sigma factor for heat-shock promoters." Cell 38:383-390 (1984); Grossman, A. D. et al., "Analysis of Escherichia coli heat shock response," p. 327-331, in L. L. Lieve (ed.), Microbiology—1985, American Society for Microbiology, Washington, D.C. (1985); and Grossman, A. D. et al., "$\sigma^{32}$ synthesis can regulate the synthesis of heat shock proteins in Escherichia coli", Genes Dev. 1:179-184 (1987); and reviewed by Helmann, J. D. et al. in "Structure and function of bacterial sigma factors." Annu. Rev. Biochem. 57:839-872 (1988); which publications are incorporated herein by reference. Escherichia coli cell growth at temperatures above 20° C. requires the $\sigma^{32}$ protein. Induction of heat shock gene expression is caused by a 20-fold increase in the amount of $\sigma^{32}$ protein, resulting in exclusive transcription initiation from the heat shock gene promoters. Since the $\sigma^{32}$ protein is relatively unstable, prolonged heat shock gene expression requires continual synthesis of $\sigma^{32}$ protein. The heat shock proteins DnaK, DnaJ, and GrpE have been shown to negatively regulate heat shock gene expression by controlling the synthesis and stability of $\sigma^{32}$. See Straus, D. B. et al., "DnaK, DnaJ, and GrpE heat shock proteins negatively regulate heat shock gene expression by controlling the synthesis and stability of $\sigma^{32}$." Genes Dev. 4:2202-2209 (1990).

Under permissive growth conditions (i.e., approximately 46° C. or lower), the rpoH gene is transcribed from four tandem promoters, P1, P3, P4, and P5. Promoters P1, P4, and P5 are transcribed by RNA polymerase containing $\sigma^{70}$ protein, the major sigma factor, and function at nonlethal temperatures. At lethal temperatures (e.g., 50° C.), transcription of the rpoH gene occurs solely at P3 by RNA polymerase holoenzyme containing a novel sigma factor, $\sigma^E$.

Mutations in the rpoH gene which curtail heat shock gene expression have been characterized. Such mutants might have practical value for synthesis of heterologous proteins because inhibition of the heat shock response causes an overall decrease in proteolysis. Besides protease La, other heat shock proteins have been implicated in proteolysis, including Clp, DnaK, DnaJ, GrpE, and GroEL. The precise functioning of DnaK, DnaJ, GrpE, and GroEL in proteolysis is still not well defined. As opposed to proteases La and Clp, it is doubtful that DnaK, DnaJ, GrpE, and GroEL are actual proteases. Rather, they appear to mediate proteolysis indirectly by yet undetermined mechanisms, perhaps involving folding/assembly. Heat shock proteins implicated in proteolysis (i.e., La, Clp, DnaK, DnaJ, GrpE, and GroEL) are synthesized at decreased rates in rpoH mutants. The most commonly used rpoH mutant allele, rpoH165, is an amber mutation that renders the cell temperature-sensitive for growth which is described in Cooper, S. et al., "A Temperature Sensitive Nonsense Mutation Affecting the Synthesis of a Major Protein of Escherichia coli K12", Molec. Gen. Genet. 139:167-176 (1975). Nearly all of the other rpoH mutant alleles characterized also provides a temperature-sensitive phenotype.

Mutations in the lon or rpoH gene phenotypically suppress a temperature-sensitive mutation in the $\sigma^{70}$ protein subunit of RNA polymerase (rpoD800/rpoD285 mutant allele) at high temperature. The phenotypic suppression by lon or rpoH mutants at high temperature has been found to be due to decreased proteolysis of the mutant, labile $\sigma^{70}$ protein. Of the four characterized rpoH mutants selected as temperature-resistant suppressor mutants of an rpoD800 strain, only one was found to be temperature-resistant in an rpoD+ background. As used herein, a superscript "+" designates a wild-type gene. The rpoD gene is described in Helmann, J. D. et al., supra; and Yura, T. et al., "Genetic studies of RNA polymerase $\sigma$ factor in E. coli," p. 51-63, in Osawa, S. et al. (ed.) Genetics and Evolution of RNA Polymerase, tRNA, and Ribosomes. Univ. of Tokyo Press, Tokyo, Japan; which publications are incorporated herein by reference. The rpoD800 gene has been described by Hu, J. et al. in "Marker rescue with plasmids bearing deletions in rpoD identifies a dispensable part of E. coli $\sigma$ factor." Mol. Gen. Genet. 191:492-298 (1983), while mutations in the lon or rpoH gene which suppress the rpoD800 mutation have been described by Grossman, A. D. et al. in "Mutations in the lon gene of E. coli K12 phenotypically suppress a mutation in the sigma subunit of RNA polymerase," Cell 32:151-159 (1983), and by Grossman, A. D. et al. in "Mutations in the rpoH (hptR) gene of Escherichia coli K-12 phenotypically suppress a temperature-sensitive mutant defective in the sigma-70 subunit of RNA polymerase," J. Bacteriology 161:939-943 (1985).

Thus, one drawback with using rpoH mutant strains is that the choice of mutant alleles is limited and a temperature shift to the non-permissive temperature, 42° C., must be performed to maximize heterologous protein accumulation. Nonetheless, the use of rpoH mutant strains, particularly rpoH lon double mutants, has been reported to increase heterologous protein accumulation levels. Examples include IGF-1 and unstable derivatives of λ repressor protein.

Conventionally, it is understood that altered rpoH genes that provide enhanced heterologous protein accumulation do so by decreasing proteolysis. Thus, for example, it has been reported recently in Goldberg, et al PCT/US89/03839, international application no. WO 90/03438, published Apr. 5, 1990, that an altered rpoH gene, rpoH165(am), has been discovered to result in improved heterologous gene expression by retarding proteolysis. Accordingly, researchers are still seeking to isolate and to characterize hitherto unknown rpoH mutations which result in higher accumulation levels of heterologous proteins. Also, it is important to identify an rpoH mutation which still confers desirable fermentation properties on the strain for optimal productivity of heterologous proteins, including 1) cell viability coupled with a relatively fast growth rate within a range of temperatures (e.g., 25°-42° C.), 2) lack of a mucoid phenotype characteristic of lon mutants, and 3) enhanced accumulation of various heterologous proteins without performing a temperature shift. The novel rpoH mutants described below possess all of these desired attributes.

SUMMARY OF THE INVENTION

Briefly, therefore, the present invention is directed to a newly isolated mutant rpoH gene that encodes an altered $\sigma^{32}$ protein in which cysteine instead of arginine is at amino acid residue 268.

The present invention is also directed to an isolated rpoH gene in which thymine instead of cytosine is at the nucleotide position corresponding to 802 in the rpoH+ gene.

The present invention is additionally directed to a purified strain of E. coli containing such an rpoH gene.

The present invention is also directed to a method for synthesis of protein. The method comprises introducing an expression vehicle into an E. coli strain containing the mutant rpoH gene of this invention.

Among the several advantages of the invention, therefore, may be noted the provision of E. coli strains that are viable at the maximum growth temperature of the parental rpoH+ strain; the provision of such strains that are useful in synthesizing protein at enhanced accumulation levels at temperatures above 20° C.; the provision of an isolated mutant rpoH gene that imparts such characteristics to E. coli strains; the provision of such genes that are rpoD+ compatible (i.e., viable in an rpoD+ strain background); and the provision of a method for enhancing accumulation of heterologous or homologous proteins.

DETAILED DESCRIPTION OF THE PREFERRED EMBODIMENT

In this specification, the following abbreviations, notations and phrases are used. The use of the superscript "+" designates a wild-type gene. For example, rpoH+ refers to the wild-type rpoH gene. The phrase "expression vehicle" describes a unit that, when added to a host organism, replicates and expresses a gene of interest. Thus, an expression vehicle may be chromosomal or non-chromosomal DNA comprising an intact replicon such that the vehicle is replicated when placed within a host organism. Desired protein may be synthesized by introduction of an expression vehicle to a host organism. The phrase "transcriptional unit" refers to that part of a replicon that controls expression of the gene of interest, regardless of whether the expression vehicle bearing the transcriptional unit is a plasmid-based expression vehicle, a phage-based expression vehicle, a transposon/insertion sequence-based expression vehicle or some other type of vehicle. Referring to a gene as being "compatible" with another gene means that a cell remains viable when containing the combination of the two genes. As used herein, the phrase "enhanced accumulation" refers to the fact that under at least certain conditions (and typically a wide range of conditions), protein accumulation levels resulting from the introduction of transcriptional units into the species of this invention are higher than resulting from introduction of the same transcriptional units into the corresponding prior art species (i.e., species containing an rpoH gene encoding arginine at amino acid residue 268) under the same conditions. The designation "rpoH358" has been given to the isolated gene of this invention. References herein to nucleotide positions are based on a numbering scheme in which A of the ATG initiator codon is assigned +1. As used herein, the phrase "purified strain" describes a strain that has been purified from a whole population. Explanations of other notations, abbreviations and phrases will be provided in the following text.

In accordance with the present invention, it has been discovered that E. coli containing a particular newly isolated mutant rpoH gene results in a temperature-resistant phenotype in an rpoD+ strain background and, when employed in protein synthesis, results in significantly enhanced accumulation levels of whatever proteins are being synthesized. In this respect, such enhanced accumulation has been found for several heterologous proteins; and with respect to one heterologous protein, such enhanced accumulation has been found to result regardless of the promoter employed.

Accordingly, for Arg(CGC) at amino acid residue 268, a single alteration, a C>T transition at nucleotide position 802 of the rpoH gene, encodes a protein having the amino acid sequence of $\sigma^{32}$ protein, except having cysteine (Cys) instead of arginine (Arg) at amino acid residue 268, and has been found to sustain growth at the maximum growth temperature of the parental rpoH+ strain and to result in enhanced heterologous protein accumulation as well. Moreover, in contrast to most rpoH mutations, the rpoH mutation of this invention, designated rpoH358, has been found to be compatible with the rpoD+ gene. Thus, viable strains bearing the combination rpoH358 rpoD+ have been developed. In addition, such strains bear a functional heat shock response.

As noted, it has been reported that rpoH mutants that provide enhanced heterologous protein accumulation do so by decreasing proteolysis, as in Goldberg, supra. Yet, surprisingly, it has been discovered that protein half-life associated with the rpoH358 gene of the present invention is indistinguishable from that associated with the rpoH+ gene. Instead, it has been found that with respect to the rpoH358 gene of this invention, increased protein accumulation is related not to decreased proteolysis, but to increased synthesis of the respective heterologous protein, presumably resulting from the observed increased levels of the respective heterologous mRNA.

Thus, in summary, the rpoH358 gene is compatible with the rpoD+ gene, provides a temperature-resistant phenotype which allows cell growth at the maximum temperature permitted by the parental rpoH+ strain (e.g., 46° C. for W3110), possesses an apparently fully functional heat shock response and causes increased accumulation levels of several heterologous proteins. Increased accumulation was found specifically for the prohormone of human atrial natriuretic factor (pro-ANF), human and bovine insulin-like growth factor-1 (IGF-1; human and bovine IGF-1 are identical), bovine insulin-like growth factor-2 (bIGF-2), bovine placental lactogen (bPL) and bovine prolactin (bPRL). However, it is believed that enhanced accumulation is not limited to such proteins, but would accompany synthesis of any heterologous or homologous protein.

Moreover, it is believed that in any technique for maximizing expression of heterologous or homologous genes by means of E. coli, by simply utilizing the rpoH358 gene of this invention in place of the rpoH+ gene will result in enhanced heterologous or homologous (as desired) protein accumulation. In particular, in expression systems where transcription is initiated by a promoter, the benefits attained by the use of the rpoH358 gene of this invention have been found to be promoter-independent.

Briefly, and as will be described in more detail in the examples below, the rpoH358 gene of this invention was isolated as follows. Extragenic temperature-resistant suppressor mutants of an rpoD800 derivative of W3110 were selected and the resulting mutant colonies were purified. W3110 is described in Bachmann, B. J., "Derivations and genotypes of some mutant derivatives of *Escherichia coli* K-12," p.1190–1219, in Neidhardt, F. C. et al. (ed.), *Escherichia coli and Salmonella typhimurium*, American Society for Microbiology, Washington, D.C. (1987). Genetic mapping of two of the mutants (which were later determined to have the same mutation in the rpoH gene, designated rpoH358) showed that the mutation conferring temperature resistance resided in the rpoH gene. P1-mediated transduction of the rpoD+ gene into the two rpoD800 rpoH358 mutants resulted in viable rpoH358 mutants that retained temperature resistance at 46° C., the maximum growth temperature of W3110. The complete rpoH358 gene, including the regulatory region, from the two mutants (designated MON102 and MON105) and parental W3110 was cloned and sequenced. Thus, the rpoH358 gene was isolated and DNA sequencing results showed that a single C>T transition was present in the rpoH gene from both MON102 and MON105, resulting in an Arg(CGC)>Cys(TGC) substitution at amino acid residue 268 (R-268-C, designated rpoH358). In such notation, Arg represents arginine, Cys represents cysteine, C represents cytosine, G represents guanine, and T represents thymine.

Specifically, purified strains of E. coli containing the rpoH358 gene were prepared as follows. Following P1-mediated transduction, an rpoD800 derivative of E. coli strain W3110 was selected for tetracycline resistance encoded by a Tn10 element that maps closely to rpoD800. Such association is described by the notation "rpoD800-Tn10". Tetracycline-resistant transductants were then scored for temperature sensitivity, resulting in an rpoD800-Tn10 derivative designated MON100, which was then used to select for extragenic temperature-resistant mutants at 43.5° C., resulting in two mutants, designated MON101 and MON104, that had an rpoD800-Tn10 rpoH358 genotype. The technique for such a selection is described by Grossman, A. D., et al., in "Mutations in the rpoH (htpR) gene of *Escherichia coli* K-12 phenotypically suppress a temperature-sensitive mutant defective in the sigma-70 subunit of RNA polymerase," *J. Bacteriology* 161:939–943 (1985). Strain MON100 contains a Tn10 element encoding tetracycline resistance approximately 90% linked to rpoD800. Direct, positive selection for loss of Tn10-encoded tetracycline resistance in MON101 and MON104 was carried out by plating approximately $10^5$–$10^6$ cells on a modified fusaric acid-containing medium at 37° C. The technique is described by Maloy, S. R. and Nunn, W. D., in "Selection for loss of tetracycline resistance by *Escherichia coli*," *J. Bacteriology* 145:1110–1112 (1981). Fusaric acid-resistant colonies which were tetracycline-sensitive and still retained temperature resistance at 43.5° C. arose at a frequency of approximately $10^{-4}$. One representative tetracycline-sensitive, temperature-sensitive derivative of MON101 and MON104 (designated MON103 and MON106, respectively) was picked and used for mapping and further strain construction.

The rpoD+ gene from W3110 was then transduced by P1-mediated transduction into the rpoD800-Tn10 rpoH358 mutants, MON101 and MON104, by selecting for transductants at 46° C. (a non-permissive temperature for the rpoD800-Tn10 rpoH358 mutants), thereby resulting in rpoD+ rpoH358 derivatives designated MON102 and MON105 (relating to MON101 and MON104, respectively). A culture of the respective E. coli temperature-resistant transductant was purified and, as expected, was tetracycline-sensitive due to the loss of the Tn10 element during P1-mediated transduction of rpoD800-Tn10 to rpoD+. A culture of MON105 has been deposited with the ATCC and has been assigned deposit accession no. ATCC 55204.

The strains thus identified are summarized in Table I:

TABLE I

Bacterial Strains

| Strain | Genotype | Source/Reference |
|---|---|---|
| CAG1130 | F-thil thr1 leu6 lacY1 tonA21 supE44 galk rpoD800-Tn10 | C. Gross, U. of Wisconsin; rpoD800-TN10 derivative of C600; Tn10 approximately 90% linked to rpoD800 |
| CAG440 | lac(am) trp(am) pho(am) supC$^{ts}$ rpsL mal(am) lon+ rpoH+ | C. Gross, U. of Wisconsin |
| CAG630 | lac(am) trp(am) pho(am) supC$^{ts}$ rpsL mal(am) lon+ rpoH165(am)-Tn10 | C. Gross, U. of Wisconsin; Tn10 approximately 85% linked to rpoH165(am) |
| W3110 | F-λ-IN (rrnD-rrnE)1 | Bachmann, B. J. 1987. Derivations and genotypes of some mutant derivatives of *Escerichia coli* K-12, p. 1190–1219 in Niedhardt *coli* and *Salmonella typhimurium*. American Society for Microbiology, Washington, D.C. |
| JM101 | Δ(prolac) supE thiA/ F'traD36 proAB lacI$^q$ lacZΔM15 | Messing, J. 1979. A multipurpose cloning system based on the single stranded DNA bacteriophage M13. Recombinant DNA Technical Bulletin, NIH Publication No. 79-99, Vol 2, pp. 43–48. |
| MON100 | rpoD800-Tn10 | P1(CAG1130) × W3110 |

TABLE I-continued

Bacterial Strains

| Strain | Genotype | Source/Reference |
|---|---|---|
| MON101 | rpoD800-Tn10 rpoH358 | Temperature resistant suppressor mutant #1 of MON100 selected at 43.5° C. |
| MON102 | rpoD+ rpoH358 | P1(W3110) × MON101 |
| MON103 | rpoD800 Δtet rpoH358 | Fusaric acid-resistant, tetracycline-sensitive derivative of MON101 |
| MON104 | rpoD800-Tn10 rpoH358 | Temperature-resistant suppressor mutant #2 of MON100 selected at 43.5° C. |
| MON105 | rpoD+ rpoH358 | P1(W3110) × MON104 |
| MON106 | rpoD800 Δtet rpoH358 | Fusaric acid-resistant tetracycline-sensitive derivative of MON104 |
| MON107 | rpoH+-Tn10 | P1(CAG630) × CAG440; tetracycline-resistant temperature-resistant transductant at 43.5° C. |
| MON108 | rpoD800 Δtet rpoH358-Tn10 | P1(MON107) × MON103; tetracycline-resistant, temperature-resistant transductant at 4.35° C. |
| MON109 | rpoD800 Δtet rpoH+-Tn10 | P1(MON107) × MON103; tetracycline-resistant, temperature-resistant transductant at 43.5° C. |
| MON110 | rpoD800 Δtet rpoH358-Tn10 | P1(MON107) × MON106; tetracycline-resistant, temperature-resistant transductant at 43.5° C. |
| MON111 | rpoD800 Δtet rpoH+-Tn10 | P1(MON107) × MON106; tetracycline-resistant, temperature-resistant transductant at 43.5° C. |
| MON114 | rpoH358-Tn10 | P1(MON110) × JM101 |
| MON115 | rpoH+-Tn10 | P1(MON111) × JM101 |
| MON116 | rpoH358-Tn10 | Pa(MON110) × W3110 |
| MON117 | rpoH+-Tn10 | P1(MON111) × W3110 |

The rpoH358 gene may likewise be derived by other processes, such as standard site-directed mutagenesis techniques. Specifically, either cysteine codon, UGC or UGU, where U represents uracil, may be derived by such techniques.

The altered $\sigma^{32}$ protein encoded by the rpoH358 gene of this invention has an Arg>Cys substitution at nucleotide 802 in which beneficial results including rpoD+ compatibility, temperature resistance at the maximum growth temperature of the parental rpoH+ strain, a functional heat shock response and enhanced protein accumulation are attained. Further, as noted, the enhanced protein accumulation associated with this substitution is not related to decreased proteolysis.

Moreover, it should be recognized that the protein may have other differences from $\sigma^{32}$ protein besides the noted distinction at amino acid residue 268, just as the rpoH358 gene may differ from the rpoH+ gene at places besides nucleotide 802. Thus, substitutions at other amino acid residues or amino acid insertions or deletions may be made as desired. Therefore, while protein of this invention may have the exact amino acid sequence of $\sigma^{32}$ protein with the sole exception of the amino acid substitution at residue 268, other substitutions at other amino acid residues or amino acid insertions or deletions may be made without departing from the scope of this invention. Likewise, the rpoH358 gene of this invention may include other alterations besides the C>T substitution at nucleotide 802, which results in the substitution of Arg>Cys at amino acid residue 268. Moreover, although such alterations might result in shifts of nucleotide or amino acid sites, references herein to nucleotide 802 or amino acid 268 refers to the nucleotide or amino acid present at positions 802 or 268, respectively, in an unaltered gene or protein, respectively.

Enhanced accumulation of heterologous proteins has been demonstrated in strains containing the rpoH358 gene of this invention by the introduction of plasmids as expression vehicles for heterologous protein synthesis. However, it is believed that enhanced accumulation of homologous proteins as well can be achieved by use of mutant strains containing the rpoH358 gene of this invention, specifically E. coli containing such gene in place of the rpoH+ gene in any expression system utilizing such genes or bacteria to enhance synthesis of heterologous or homologous proteins. The enhanced accumulation of heterologous proteins has not been found to be dependent upon the promoter. Thus, any promoter, whether constitutive or inducible, which functions in E. coli is believed to be suitable. In particular, the recA or araBAD promoter, used in conjunction with the phage T7 gene 10L ribosome binding site, showed that increased accumulation levels were obtained with a number of representative heterologous proteins tested in the W3110 rpoH358 mutants, MON102 and MON105, compared to parental W3110. Similarly, enhanced heterologous protein accumulation has been obtained with an rpoH358 derivative of JM101 (referred to as MON114), compared to parental JM101, showing that the rpoH358 gene functions in an analogous manner in a strain background different from W3110.

Generally, enhanced accumulation of heterologous proteins has been obtained, regardless of the type of protein synthesized. However, it is difficult to further enhance already high levels of accumulation. Accordingly, enhanced accumulation is particularly remarkable with respect to those proteins ordinarily associated with lower levels of accumulation. In particular, improvements of from about 800% to about 50% in accumulation have been noted with insulin-like growth factor-1 (IGF-1), bovine insulin-like growth factor-2 (bIGF-2), prohormone of human atrial natriuretic factor (pro-ANF), bovine placental lactogen (bPL) and bovine prolactin (bPRL).

Thus, any protein may be synthesized according to standard techniques, but with the rpoH358 gene or strains of this invention in place of the conventional genes or strains. Accordingly, any expression system such as plasmid expression vehicles, chromosomal-type expression vehicles, phage-based expression vehicles or transposon/insertion sequence-based expression vehicles may be employed. Generally, the expression vehicle is introduced into a host strain of E. coli containing the rpoH358 gene of this invention. The expression vehicle contains a transcriptional unit, which typically comprises a promoter, ribosome binding site, heterologous or homologous gene to be over-expressed and a transcription terminator. The gene is selected according to the desired protein to be synthesized. It is believed that the present invention is not limited to plasmids or any particular expression vehicle or to any particular transcriptional unit or promoter, which controls expression of the desired heterologous or homologous gene.

The transcriptional unit, and in particular, the promoter, may be selected based on the same criteria applied in making such selection according to the techniques employed with prior art for E. coli-mediated expression. Thus, while plasmids such as derivatives of pBR327, which was in turn derived from pBR322, have been found to be suitable, it should be recognized that any plasmid or other expression vehicle (e.g., phage-based expression vehicle or transposon/insertion sequence-based expression vehicle) may be chosen. Likewise, although the recA and araBAD promoters have been found to be appropriate, any promoter, whether constitutive or inducible, may be employed.

Other advantages derived from the practice of this invention will be apparent from the following description and examples.

EXAMPLE 1

Selection of extragenic temperature-resistant mutants of an rpoD800 derivative of W3110 was carried out as follows. It is known that the 70 kDa sigma subunit of RNA polymerase ($\sigma^{70}$) is encoded by the rpoD gene in *E. coli* and regulates transcription initiation of promoters required for normal cell growth. Moreover, it has also been reported that the rpoD800 (also referred to as rpoD285) mutant allele has an in-frame internal deletion of 42 base pairs and gives a temperature-sensitive phenotype because the mutant $\sigma^{70}$ subunit is rapidly degraded at temperatures greater than 40° C.

Previous experiments showed that extragenic temperature-resistant suppressor mutants of strains containing the rpoD800 mutation could be obtained. In addition, the type of suppressor mutation obtained appeared to be strain dependent. Selection at 41.5° C. yielded predominantly lon mutants in strain C600, whereas selection at 43.5° C. yielded predominantly rpoH mutants in strain 285c. Selection for rpoH358 mutants in strain W3110 was carried out in an analogous manner by selecting for temperature-resistant suppressor mutants of an rpoD800 derivative of W3110 at 43.5° C.

*E. coli* cell cultures were grown in Luria-Bertani (LB) or M9 minimal medium. See Sambrook, J., et al, "Molecular Cloning: A Laboratory Manual." Cold Spring Harbor Laboratory Press, Cold Spring Harbor, N.Y. (1989). Shake flask inductions were performed by growing the cultures in M9 medium supplemented with casamino acids, thiamine, and trace minerals. See Obukowicz, M. G., et al., "Secretion and export of IGF-1 in *Escherichia coli* strain JM101." *Mol. Gen. Genet.* 215:19-25 (1988), regarding the composition of the M9 induction medium and sampling methods from shake flask inductions. For $^{35}$S-labeling of proteins, cells were grown in either $^{35}$S-methionine labeling medium or M9 induction medium ($^{35}$S-cysteine labeling). $^{35}$S-methionine labeling medium contains very low endogenous levels of methionine and consists of M9 salts plus 1 mM MgCl$_2$, 0.2% glucose, 0.05% casamino acids, 0.01% yeast extract, and 0.005% vitamin B1. M9 induction medium was used for labeling with $^{35}$S-cysteine because cysteine, unlike methionine, is absent in casamino acids.

The rpoD800 mutation was introduced into W3110 by P1vir-mediated transduction of a Tn10 element encoding tetracycline-resistance, which maps closely to rpoD800. Standard P1vir-mediated transductions were performed according to the method of Silhavy et al., *Experiments with Gene Fusions*, Cold Spring Harbor Laboratory, Cold Spring Harbor, N.Y. (1984). All transductants were single colony purified on the selective medium before testing them for their growth phenotype. Cross-streaking against λvir was also performed to confirm the absence of P1vir lysogens. Tetracycline-resistant transductants were selected and then scored for temperature sensitivity. One tetracycline-resistant, temperature-sensitive transductant of W3110 (referred to as MON100) having an rpoD800-Tn10 genotype was picked for further experimentation.

Temperature-resistant suppressor mutants from two different cultures of MON100 appeared at a frequency of approximately $10^{-7}$ on LB agar medium. Twenty-one non-mucoid colonies (five from culture no. 1 and sixteen from culture no. 2) were picked at random and single colony purified at 43.5° C. two additional times. Mucoid colonies were not chosen because of the likelihood that they were lon mutants. See Grossman et al., "Mutations in the lon gene of *E. coli* K12 phenotypically suppress a mutation in the sigma subunit of RNA polymerase," Cell 32:151-159 (1983). All five mutants analyzed from culture no. 1 and 14 out of 16 mutants analyzed from culture no. 2 retained temperature resistance. Five mutants from each culture were then assessed for enhanced accumulation levels of IGF-1 encoded by the plasmid pMON2320 and pro-ANF encoded by the plasmid pMON5589, both of which plasmids are described in Example 4 below. Higher accumulation levels of both IGF-1 and pro-ANF were obtained in two of the ten putative rpoH mutants of MON100 (designated MON101 and MON104) compared to MON100. MON101 and MON104 were derived from the same MON100 culture, making it possible that they were siblings. Even so, both mutants were characterized further by genetic mapping.

Standard Hfr, P1vir co-transductional and complementation mapping techniques showed that the mutation responsible for the temperature-resistant phenotype in MON101 and MON104 resided in the rpoH gene.

While the maximum growth temperature in which strain W3110 forms colonies on LB agar is 46° C., both MON101 and MON104 failed to form colonies at temperatures above 43.5° C.

EXAMPLE 2

In order to assess whether higher accumulation levels of heterologous proteins could be obtained in an rpoD$^+$ strain background containing the rpoH mutation and to determine whether the rpoH mutation would be compatible with the rpoD$^+$ gene (and, if so, whether it would still provide a temperature-resistant phenotype), rpoD$^+$ derivatives of MON101 and MON104 of Example 1 were constructed.

A P1vir lysate of W3110 was used to transduce rpoH$^+$ into MON101 and MON104. The rpoD$^+$ rpoH derivatives are referred to as MON102 and MON105, respectively. The rpoD$^+$ rpoH transductants, MON102 and MON105, were selected for their ability to grow and form colonies at 46° C. on LB agar, a non-permissive temperature for MON101 and MON104. Since the rpoD800 mutant allele is closely linked to a Tn10 element encoding tetracycline resistance, the loss of the tetracycline-resistant phenotype in the rpoD$^+$ rpoH transductants served to verify the presence of the rpoD$^+$ gene. Temperature-resistant, tetracycline-sensitive transductants were obtained with both recipients, indicating that the putative rpoH mutant allele was compatible with the rpoD$^+$ gene and provided a temperature-resistant phenotype.

In order to determine precisely the mutation in the rpoH gene, the entire rpoH gene, including the complex regulatory region, was isolated from the genome of the rpoD$^+$ rpoH mutants, MON102 and MON105, and from parental W3110 (rpoH$^+$) by standard polymerase chain reaction (PCR) techniques as a 1.2 kb Bam HI fragment. The entire DNA sequence of the regulatory region (approximately 0.2 kb) and the structural gene (approximately 1.0 kb) was determined on both strands by standard double-stranded plasmid DNA sequencing techniques. Results showed that the sequence of the regulatory and structural portions of the rpoH gene from parental W3110 was identical to the published sequence of the rpoH+ gene. See Calendar et al., "Deletion and insertion mutations in the rpoH gene of *Escherichia coli* that produce functional sigma-32," *J. Bacteriology* 170:3479-3484 (1988).

By contrast, the rpoH gene from the mutants, MON102 and MON105, had the identical structural gene mutation, herein referred to as the rpoH358 gene. A C>T transition was found to be present at nucleotide 802, causing an Arg(CGC)>Cys(TGC) non-homologous amino acid substitution at amino acid residue 268 (R-268-C) near the C-terminus of the $\sigma^{32}$ protein. The rpoH358 structural gene mutation in MON102 and MON105 was confirmed to be present in the rpoH gene of the original temperature-resistant suppressor mutants, MON101 and MON104, by DNA sequence analysis of a portion of the analogous 1.2 kb Bam HI fragment.

While the identical amino acid sequence was present in the altered $\sigma^{32}$ from MON102 and MON105, an additional silent mutation was also present in the rpoH gene of MON105. A T>C transition at nucleotide 555 was present, changing the UCU serine codon at amino acid 185 to a UCC serine codon. Both UCU and UCC are highly preferred *E. coli* serine codons. PCR cloning and DNA sequencing was repeated for this mutant and yielded the same result. However, DNA sequencing of the rpoH gene present in the original temperature-resistant suppressor mutant, MON104, showed that the wild-type sequence (UCU serine codon) was present. It remains unclear why a silent mutation occurred during the construction of MON105 from MON104. The relevance of this silent change is unknown, although previous reports in the literature showed there to be disagreement in the amino acid present at this position due to an altered nucleotide in the codon. See Calendar, R. et al., "Deletion and Insertion Mutation in the rpoH Gene of *Escherichia coli* that Produce Functional sigma-32", *J. Bacteriology* 170:3479-3484 (1988).

Characterization of the mutant phenotype of the altered rpoH strains, MON102 and MON135, was performed, especially with regard to the affects of an altered $\sigma^{32}$ subunit on enhanced accumulation of heterologous proteins. Ensuing results showed that MON102 and MON105 behaved identically.

EXAMPLE 3

It has been established that previously known rpoH mutants are deficient to varying degrees in inducing the heat shock response. Several heat shock proteins have been implicated in mediating directly or indirectly host cell proteolysis, including La, DnaJ, DnaK, GrpE, and GroEL. Specifically, mutations in these heat shock genes cause a decreased rate of puromycyl fragment decay. Puromycin added to actively growing bacterial cultures causes premature translation termination, generating unstable puromycyl polypeptides. The rate of degradation of these polypeptides into trichloroacetic acid-soluble products has been used to measure the ability of strains to carry out the degradation of abnormal proteins.

Experiments examining the rate of puromycyl fragment decay were performed with the rpoH358 mutants, MON102 and MON105, and with parental W3110 in order to determine whether the rpoH358 mutation caused a decreased rate of proteolysis. Proteolysis was examined at 37° C. in cultures grown in $^{35}$S-methionine labeling medium. The results showed that there were no significant differences in the rates of proteolysis between parental W3110 and the rpoH358 mutant strains, MON102 and MON105.

No observable changes in protein synthesis were observed with the rpoH358 strains MON102 and MON105, compared to parental W3110 prior to or after induction of the heat shock response. The profile and relative amounts of newly synthesized heat shock proteins were comparable in parental W3110 and the rpoH358 mutants, MON102 and MON105, regardless of whether the cultures were maintained at 30° C. or temperature-shifted from 30° to 42° C. or from 30° to 50° C. At 50° C., heat shock proteins were synthesized exclusively.

EXAMPLE 4

The following table identifies the plasmids which were derived from pBR327 and employed in this example. Abbreviations used in the table are defined below the table.

| Plasmid | Drug Marker | Relevant Features |
| --- | --- | --- |
| pMON55819 | Ap$^R$ | PrecA-g10L-pro-ANG-T7$_{ter}$; Pro-ANF cDNA clone |
| pMON2320 | Ap$^R$ | PrecA-g10L-IGF-1-T7$_{ter}$; synthetic IGF gene with *E. Coli*-preferred codons |
| pMON2368 | Ap$^R$ | PrecA-g10L-IGF-1-flori$_{ter}$; synthetic IGF-1 gene from pMON2320 that is A-T-rich in first 14 codons to PstI site. |
| pMON2360 | Ap$^R$ | PrecA-g10L-bIGF-2-flori$_{ter}$; synthetic IGF-2 gene that is A-T-rich in first 16 codons to PstI site |
| pMON3403 | Sp$^R$ | PrecA-g10L-bPL-T7$_{ter}$; bPL cDNA clone |
| pMON3859 | Ap$^R$ | PrecA-g10L:40-bPRL:4-flori$_{ter}$; g10L:40 has A-T-rich spacer region between the SD sequence and AUG initiator codon and a C nucleotide at position −5; bPRL:4 is the bPRL cDNA clone with the first 10 codons made A-T-rich |
| pMON3843 | Ap$^R$ | ParaBAD-g10L:40-bPRL:4-flori$_{ter}$; ParaBAD derivative of pMON3859 |

Abbreviations: Ap$^R$ refers to ampicillin resistance; bPL refers to bovine placental lactogen; bPRL refers to bovine prolactin; flori$_{ter}$ refers to phage f1 ori transcription terminator sequence; g10L refers to phage T7 gene 10 leader sequence; IGF-1 refers to insulin-like growth factor-1; bIGF-2 refers to bovine insulin-like growth factor-2; ParaBAD refers to the araBAD promoter; PrecA refers to the recA promoter; pro-ANF refers to prohormone of atrial natriuretic factor; Sp$^R$ refers to spectinomycin resistance; T7$_{ter}$ refers to phage T7 gene 10 transcription terminator sequence.

The following table identifies references further describing the heterologous gene and/or corresponding expression plasmid.

| Plasmid | Reference |
|---|---|
| pMON5589 | Gierse, J. K., et al., "Expression, purification, and in vivo activity of atrial natriuretic factor prohormone produced in *Escherichi coli*," Archiv. Biochem. Biophys., 271:441–446 (1989). |
| pMON2320 and pMON2368 | Wong, E. Y. et al., "Expression of secreted insulin-like growth factor-1 in *Escherichia coli*," Gene 68:193–203 (1988). |
| pMON2360 | Easton, A. M., et al., "Production of bovine insulin-like growth factor-2 (bIGF-2) in *Escherichia coli*," Gene, 101:291–295 (1991). |
| pMON3403 | Schuler, L. A., et al., "Bovine placental lactogen: molecular cloning and protein structure." Biochemistry, 27:8443–8448 (1988). |
| pMON3859 and pMON3843 | Miller, W. L. et al., "Cloning of bovine prolactin cDNA and evolutionary implications of its sequence," DNA, 1:37–50 (1981). |

Results reported in the literature have shown that accumulation of heterologous proteins sometimes increases in previously known rpoH mutants. Several heterologous proteins (i.e., pro-ANF, IGF-1, bIGF-2, bPL, and bPRL) were used in combination with two unrelated promoters, recA and araBAD, in order to ascertain whether enhanced protein accumulation in the rpoH358 mutants, MON102 and MON105 of Example 2, was heterologous protein-independent and promoter-independent. Not all of the heterologous proteins tested were totally unrelated. IGF-1 and bIGF-2 have approximately 60% homology, whereas bPL and bPRL have approximately 50% homology. However, there is no similarity between pro-ANF, IGF-1/bIGF-2, and bPL/bPRL. The recA promoter is a relatively strong $\sigma^{70}$-dependent promoter that has strong consensus in the −35 and −10 regions with other $\sigma^{70}$-dependent promoters. In contrast, the araBAD promoter is unrelated to other $\sigma^{70}$-dependent promoters in that it lacks any recognizable consensus sequence at both the −35 and −10 regions. Instead, transcription is regulated positively and negatively by the AraC protein.

Enhanced accumulation of all of the heterologous proteins was obtained in the rpoH358 mutants, MON102 and/or MON105, compared to parental W3110. Ten Klett unit equivalents of cells were loaded per lane. Except for IGF-1, all of the heterologous proteins were detected as distinct, inducible bands by Coomassie blue-stained protein gel analysis. The identity of the inducible bands as the given heterologous proteins was confirmed by Western blot analysis or N-terminal amino acid sequencing. The accumulation levels of IGF-1 were too low to be detected by Coomassie blue-stained protein gel analysis. Instead, IGF-1 accumulation levels were estimated by Western blot analysis. The recA promoter was used to induce transcription of the genes encoding pro-ANF (pMON5589), IGF-1 (pMON2368), bIGF-2 (pMON2360), and bPL (pMON3403). The araBAD promoter was used to induce transcription of the gene encoding bPRL (pMON3843) in order to illustrate that enhanced heterologous protein accumulation in the rpoH358 mutants, MON102 and MON105, was not recA promoter-dependent. Densitometric scanning of a representative Coomassie blue-stained protein gel or Western blot was used to quantify the relative amount of heterologous protein which accumulated post-induction. In each case, the amount of heterologous protein which accumulated to the highest level in parental W3110 was arbitrarily set at 1.0. With every heterologous protein, the results were reproducible in that consistently higher accumulation levels of the various heterologous proteins were obtained in the same relative amount in the rpoH358 mutants, MON102 and/or MON105, compared to parental W3110.

The differences in accumulation levels depended on the heterologous protein and the sampling time. IGF-1 encoded by plasmid pMON2368, characterized by a PrecA-g10L-IGF-1-flori$_{ter}$ transcriptional unit (synthetic IGF-1 gene described by Wong, et al., supra, that is A-T-rich in the first 14 codons to the PstI site) accumulated to levels approximately 8-fold higher at 2 hours following induction. In particular, Western blot analysis showed the significantly enhanced accumulation level of the heterologous protein, IGF-1, in the rpoH358 strains of this invention, MON102 and MON105, relative to parental W3110, wherein pre-induction analyses, analyses taken 30 minutes post-induction and analyses taken 2 hours post-induction were examined and compared to IGF-1 standards representing 25 ng, 50 ng and 100 ng.

bIGF-2 encoded by plasmid pMON2360 characterized by a PrecA-g10L-bIGF-2-flori$_{ter}$ transcriptional unit (synthetic bovine IGF-2 gene that is AT-rich in the first 14 codons to the PstI site) accumulated to levels approximately 1.5-fold higher at 3 hours following induction. In particular, Coomassie blue-stained protein gel analysis showed enhanced accumulation levels of the heterologous protein, bIGF-2, in the rpoH358 strain, MON102, of this invention relative to parental W3110, wherein pre-induction analyses, analyses taken 2 hours post-induction and analyses taken 3 hours post-induction were examined.

bPL encoded by plasmid pMON3403 characterized by a PrecA-g10L-bPL-T7$_{ter}$ transcriptional unit accumulated to levels approximately 2-fold higher at 4 hours following induction. In particular, Coomassie blue-stained protein gel analysis showed enhanced accumulation levels of the heterologous protein, bPL, in the rpoH358 strains, MON102 and MON105 of this invention, relative to parental W3110, wherein pre-induction analyses, analyses taken 30 minutes post-induction, analyses taken 2 hours post-induction and analyses taken 4 hours post-induction were examined.

The araBAD promoter, as well as the recA promoter, was used to control expression of bPRL. Under araBAD promoter control, bPRL encoded by plasmid pMON3843, characterized by a ParaBAD-g10L:40-bPRL:4-flori$_{ter}$ transcriptional unit, accumulated to levels approximately 2-fold higher at 2 hours post-induction, showing that enhanced heterologous protein accumulation was not specific for recA promoter-controlled expression. In particular, Coomassie blue-stained protein gel analysis showed enhanced accumulation levels of the heterologous protein, bPRL, in the rpoH358 strains, MON102 and MON105 of this invention, relative to parental W3110, wherein analyses taken 30 minutes post-induction, analyses taken 2 hours post-induction and analyses taken 4 hours post-induction were examined. By contrast, bPRL encoded by a similar plasmid, but having recA promoter control, accumulated to similar levels in the rpoH358 mutants, MON102 and MON105, and parental W3110, presumably because high-level accumulation (approximately 30% of total cell protein) was readily obtained in parental W3110.

pro-ANF encoded by plasmid pMON5589 characterized by a PrecA-g10L-pro-ANF-T7$_{ter}$ transcriptional unit accumulated to levels approximately 2-fold higher at 2 hours post-induction. In particular, Coomassie blue-stained protein gel analysis showed enhanced accumulation levels of the heterologous protein, pro-ANF, in the rpoH358 strains, MON102 and MON105 of this invention, relative to parental W3110, wherein pre-induction analyses and analyses taken 2 hours post-induction were examined.

EXAMPLE 5

Pulse-chase, Northern blot, and plasmid copy number analyses were performed to assess whether enhanced heterologous protein accumulation in the rpoH358 mutants, MON102 and MON105, occurred by decreased proteolysis or by increased synthesis and whether gene dosage (i.e., plasmid copy number) was affected. Plasmids corresponding to those identified in Example 4, above, were employed. Based on previous reports in the literature, it was presumed that increased heterologous protein accumulation levels in the rpoH358 mutants, MON102 and MON105, would be due to increased protein half-life. At the outset, this explanation was not supported by the observation that the rate of puromycyl fragment degradation was the same in MON102, MON105, and parental W3110 at 37° C., the temperature normally used for induction of heterologous gene expression.

Pulse-chase experiments were performed to compare the relative synthesis levels and half-lives of IGF-1, bPL, and pro-ANF in the rpoH358 mutants, MON102 and MON105, and parental W3110.

IGF-1 expression from pMON2368, bPL expression from pMON3403, and pro-ANF expression from pMON5589 were induced from the recA promoter by the addition of nalidixic acid. After 30 minutes, the cells were labeled with $^{35}$S-cysteine for five minutes (0 time point) and then chased with cold cysteine for the indicated times. Ten Klett unit equivalents of cells were loaded per lane. For IGF-1 and pro-ANF, the relative synthesis rates at the 0 time point and the relative protein levels during the chase were quantified by densitometric scanning of the autoradiograms. Since bPL was very stable after a 32 minute chase, only the relative synthesis rates were quantified by densitometric scanning. For the given heterologous protein, the relative synthesis rate (0 time point) in the parental strain, W3110, was arbitrarily assigned a value of 1.0. Coomassie blue staining of the protein gel prior to autoradiography showed that all of the lanes had approximately equal loadings of cell protein.

Densitometric quantification of the autoradiograms showed that the relative synthesis level of all three proteins was 1.3–1.7-fold higher in the rpoH358 mutants, MON102 and/or MON105, than in parental W3110. In particular, autoradiograms showed comparisons of the relative synthesis rate and half-life of IGF-1 in parental W3110 and the rpoH358 mutant, MON105, comparisons of the relative synthesis rate and half-life of bPL in parental W3110 and the rpoH358 mutants, MON102 and MON105, and comparisons of the relative synthesis rate and half-life of pro-ANF in parental W3110 and the rpoH358 mutant, MON105. Analyses taken at initial synthesis (0 time point), and after a 1 minute chase, a 2 minute chase, a 4 minute chase, an 8 minute chase, a 16 minute chase, and a 32 minute chase were examined. Densitometric quantification of the autoradiograms showed no differences in the half-lives of all three proteins when synthesized in the rpoH358 mutants, MON102 and/or MON105, or parental W3110. In contrast to the relative lability of IGF-1 and pro-ANF, bPL was very stable in all three strains, showing very little degradation after a 32 minute chase.

Comparisons were made of the relative mRNA levels of IGF-1 and bPL in the rpoH358 mutants, MON102 and MON105, and parental W3110. IGF-1 and bPL mRNA were detected by Northern blot analysis. The relative mRNA level from each sample was normalized to the corresponding level of 16S rRNA. The relative amount of mRNA which was present at the highest steady-state level in parental W3110 was arbitrarily set at 1.0.

Northern blot results showed that both IGF-1 and bPL mRNA levels were higher in the rpoH358 mutants, MON102 and MON105, than in parental W3110. IGF-1 mRNA levels were approximately 4-fold higher at 30 minutes following induction and approximately 2-3-fold higher at 2 hours following induction. In particular, an autoradiogram showed a comparison of the relative mRNA levels of IGF-1 in parental W3110 and the rpoH358 mutants, MON102 and MON105, wherein analyses taken 30 minutes post-induction and analyses taken 2 hours post-induction were examined. bPL mRNA levels were similar at 30 minutes following induction, but were nearly 3-fold higher at 2 hours following induction. In particular, an autoradiogram showed a comparison of the relative mRNA levels of bPL in parental W3110 and the rpoH358 mutants, MON102 and MON105, wherein analyses taken 30 minutes post-induction and analyses taken 2 hours post-induction were examined. Increased plasmid copy number did not appear to be responsible for the increased IGF-1 and bPL mRNA levels. The plasmid copy number of pMON2368 (IGF-1 expression) and pMON3403 (bPL expression) remained unaltered in the rpoH358 mutants, MON102 and MON105, and parental W3110 prior to induction and at 30 minutes, 2 hours, and 4 hours following induction. At every sampling point in all three strains, the difference in ethidium bromide fluorescence of the pMON2368 or pMON3403 samples was ≦10%.

These results suggested that for pro-ANF, IGF-1 and bPL, increased synthesis and not increased half-life resulted in increased accumulation levels in the rpoH358 mutants, MON102 and MON105, compared to parental W3110. The Northern blot results suggested that increased synthesis of IGF-1 and bPL in the rpoH358 mutants, MON102 and MON105, may, in part or totally, be due to increased mRNA levels.

EXAMPLE 6

By using a Tn10 element (zhg::Tn10) that maps closely to the rpoH gene (approximately 85% linkage), the rpoH358 allele was cotransduced into JM101 and W3110 by selecting for tetracycline-resistant transductants. JM101 is described in Messing, J., "A multipurpose cloning system based on the single stranded DNA bacteriophage M13." Recombinant DNA Technical Bulletin, NIH Publication No. 79-99, Vol. 2, pages 43-48 (1979) (See Table I). Since the rpoH358 allele provides no phenotype in rpoD+ hosts, the presence of rpoH358 in tetracycline-resistant transductants of JM101 and W3110 was confirmed by DNA sequence analysis. Single-stranded template DNA used for sequencing was prepared directly from the chromosome of tetracycline-resistant transductants by standard asymmetric PCR techniques, eliminating the intermediate step of cloning into a plasmid or phage M13. Accumulation levels of pro-ANF and IGF-1 were approximately two-three-fold higher in rpoH358-Tn10 transductants of previously unmanipulated strains of JM101 and W3110 (MON114 and MON116, respectively; see Table I for identification) compared to rpoH+-Tn10 control transductants of JM101 and W3110 (MON115 and MON117, respectively; see Table I for identification). In particular, Coomassie blue-stained protein gel analysis and Western blot analysis showed enhanced accumulation of pro-ANF and IGF-1, respectively, in MON114 and MON116 relative to MON115 and MON117. For both pro-ANF and IGF-1, pre-induction analysis of MON114, analysis of MON114 taken 2 hours post-induction, pre-induction analysis of MON115, analysis of MON115 taken 2 hours post-induction, pre-induction analysis of MON116, analysis of MON116 taken 2 hours post-induction, pre-induction analysis of MON117 and analysis of MON117 taken 2 hours post-induction were examined. The "reverse" experiment also demonstrated that rpoH358 is necessary for enhanced accumulation of heterologous proteins. The rpoH358 allele in the original rpoD800 rpoH358 derivatives of W3110, MON101 and MON104 (temperature-resistant phenotype), was converted to rpoH+ (temperature-sensitive phenotype) by P1vir-mediated co-transduction using a P1 lysate derived from an rpoH+ zhg::Tn10 donor strain (MON107; see Table I for identification). The rpoD800 rpoH+-Tn10 transductants derived from MON101 and MON104 are referred to as MON109 and MON111, respectively, whereas the corresponding rpoD800 rpoH358-Tn10 transductants are referred to as MON108 and MON110, respectively. See Table I for identification of MON108, MON109, MON110 and MON111. As expected, accumulation levels of pro-ANF were several-fold higher in MON108 and MON110 compared to MON109 and MON111. In particular, Coomassie blue-stained protein gel analysis showed enhanced accumulation of pro-ANF in MON108 and MON110 relative to MON109 and MON111, wherein analyses taken pre-induction at 30° C., 2 hours post-induction at 30° C. and 2 hours post-induction at 37° C., respectively, of MON108 and MON110, and analyses taken pre-induction at 30° C., 2 hours post-induction at 30° C. and 2 hours post-induction at 37° C., respectively, for MON109 and MON111 were examined.

As various changes could be made in the above methods and compositions without departing from the scope of the invention, it is intended that all matter contained in the above description shall be interpreted as illustrative and not in a limiting sense.

What is claimed is:

1. An isolated rpoH gene that encodes a $\sigma^{32}$ protein in which cysteine instead of arginine is at amino acid residue 268.

2. The isolated rpoH gene as set forth in claim 1 in which thymine instead of cytosine is at nucleotide position 802.

3. The isolated rpoH gene as set forth in claim 2 that is compatible with a wild-type rpoD gene.

4. A purified strain of *E. coli* having a mutant rpoH gene in which thymine instead of cytosine is at nucleotide position 802.

5. The purified strain as set forth in claim 4, wherein the mutant rpoH gene imparts to the strain enhanced protein accumulation.

6. The purified strain as set forth in claim 5, wherein the mutant rpoH gene is compatible with a wild-type rpoD gene.

7. The purified strain as set forth in claim 6, wherein the mutant rpoH gene imparts to the strain (a) temperature resistance at the maximum growth temperature of an E. coli strain with a wild-type rpoH gene and (b) a functional heat shock response.

8. The purified strain as set forth in claim 4 in which the *E. coli* strain is W3110.

9. The purified strain as set forth in claim 4 in which the *E. coli* strain in JM101.

* * * * *